(12) United States Patent
Healey

(10) Patent No.: US 7,716,843 B2
(45) Date of Patent: May 18, 2010

(54) INTEGRATED X-RAY MEASUREMENT TOOL FOR EQUINE CONFORMATION

(76) Inventor: Pete Healey, 1489 W. Hwy 154, Santa Ynez, CA (US) 93460

(*) Notice: Subject to any disclaimer, the term of this patent is extended or adjusted under 35 U.S.C. 154(b) by 82 days.

(21) Appl. No.: 11/956,179

(22) Filed: Dec. 13, 2007

(65) Prior Publication Data
US 2009/0151176 A1    Jun. 18, 2009

(51) Int. Cl.
*G06K 9/00* (2006.01)
*A01L 11/00* (2006.01)

(52) U.S. Cl. ............... 33/195; 33/511; 33/424; 33/426; 382/110; 382/286; 168/45

(58) Field of Classification Search .......... 33/1 R, 33/195, 511, 451, 471, 424, 426; 382/110, 382/286; 168/45
See application file for complete search history.

(56) References Cited

U.S. PATENT DOCUMENTS

| | | | | |
|---|---|---|---|---|
| 513,574 A | * | 1/1894 | Hayden | 33/195 |
| 583,706 A | * | 6/1897 | Kearns et al. | 33/195 |
| 616,256 A | * | 12/1898 | Platt | 33/195 |
| 832,060 A | * | 10/1906 | Holmquist | 33/195 |
| 1,585,563 A | * | 5/1926 | Schlattau | 33/471 |
| 2,000,247 A | * | 5/1935 | Niukkanen et al. | 33/454 |
| 2,039,333 A | * | 5/1936 | Musham | 33/1 R |
| 2,111,871 A | * | 3/1938 | Nissenbaum | 33/471 |
| 2,412,901 A | * | 12/1946 | McCoshen | 235/61 B |
| 3,028,679 A | * | 4/1962 | Christy | 33/354 |
| 3,270,420 A | * | 9/1966 | Simril | 33/471 |
| 5,027,520 A | * | 7/1991 | Finnegan | 33/195 |
| 7,088,847 B2 | | 8/2006 | Craig et al. | |
| 7,165,623 B2 | | 1/2007 | Healey | |
| 7,614,155 B2 | * | 11/2009 | Healey | 33/195 |
| 2008/0289199 A1 | * | 11/2008 | Healey | 33/195 |

* cited by examiner

*Primary Examiner*—Randy W Gibson
(74) *Attorney, Agent, or Firm*—Felix L. Fischer

(57) ABSTRACT

A flat transparent overlay for measurement of equine foot x-rays employs a flat lower edge for alignment with a ground surface and an anterior edge angled to approximate a hoof distal wall. A first sight ring positions the tool over a tip of an image of a third phalanx. Six interrelated scales are provided for measurement of the palmar cortex, distal sole thickness, break-over distance and coronet band to extensor process distance, and in conjunction with a second site ring, center of rotation and palmar sole thickness. A first protractor element is centered posterior on the first sight ring for measurement of the palmar angle. A dual scale extends from the angled anterior edge portion with a measurement line for measurement of the hoof-lamella zone. A second protractor element is posterior to and centered on the second sight ring for measurement of a pastern angle.

12 Claims, 8 Drawing Sheets

US 7,716,843 B2

INTEGRATED X-RAY MEASUREMENT TOOL FOR EQUINE CONFORMATION

BACKGROUND

1. Field of the Invention

This invention generally relates tools for measurements of x-ray images and more particularly to a tool integrating multiple measuring indexes in an integrated tool for evaluating equine confirmation from x-rays of the hoof.

2. Description of the Related Art

Conformation of the parasagittal section of the foot including the hoof and pastern and their internal structures often provides an indication of causes for lameness in horses. The physiology of the hoof and lower leg of the horse is well known and treatment or prevention of lameness is often effectuated through proper hoof care by a farrier. In many cases, x-rays are taken of the hoof to determine issues with conformation of the digits or other structures in the foot contributing to lameness or potential lameness of a horse. Techniques and tools for consistent imaging to allow analysis of conformation through such x-ray techniques have been developed as exemplified by those disclosed in U.S. Pat. No. 7,088,847 to Craig et al. issued Aug. 8, 2006 entitled Method and System for Analyzing Animal Digit Conformation.

Consistency and repeatability of measurement is critical in ongoing care of individual horses and for initiating shoeing programs or other treatment based on conformation of the various elements of the parasagittal section of the foot. Consistent thickness and distance measurements for the skeletal, tissue and keratinised hoof structures of the foot are necessary. At least seven critical measurements are required. Current measurement tools employing individual protractor elements and measurement scales used in current applications are cumbersome and require the use of multiple tools for obtaining necessary measurements.

It is therefore desirable to provide a single integrated tool having thickness, distance and angular measurement capability for all critical conformation measurements of the structural elements of the horse hoof.

SUMMARY OF THE INVENTION

Measuring physical parameters of the parasagittal section of an equine foot is accomplished by taking an x-ray of the parasagittal section in a side view and providing a tool with a plurality of measurement scales. A flat transparent overlay is provided with a flat lower edge for parallel alignment with a ground surface and at least a portion of an anterior edge angled at an inclination approximating a hoof distal wall. A first sight ring is provided for positioning of the tool over a tip of a third phalanx image. A first scale extends posterior at a selected angle from the first sight ring for measurement of the palmar cortex. A second scale depends from the first sight ring substantially perpendicular to the lower edge for measurement of the distal sole thickness. A third scale extends anterior perpendicular to the second scale for measurement of the break-over distance. A first protractor element is centered posterior on the first sight ring for measurement of the palmar angle. A dual scale is provided having a lower scale extending substantially radially from the first sight ring and a parallel scale upwardly spaced from the lower scale, the dual scale extends substantially perpendicular to the angled anterior edge portion and a measurement line extends between an origin on each of the lower and parallel scales for measurement of the hoof-lamella zone. A fourth scale is upwardly displaced from the first sight ring for measurement of the coronet band to extensor process distance. The fourth scale is posterior to the first sight ring and substantially perpendicular to the ground surface. A second sight ring is provided posterior to the first indicia and aligned therewith on a fifth scale having an origin at the first sight ring with the fifth scale substantially parallel to the ground surface. A sixth scale depends from the second sight ring for measurement of the palmar sole thickness. A second protractor element is posterior to and centered on the second sight ring for measurement of a pastern angle.

Measurement of the desired parameters is then accomplished by positioning the tool over the x-ray with the first sight ring aligned with the tip of P3 and the lower edge of the tool substantially aligned with the ground surface. The palmar cortex is then measured using first scale. The palmar angle is then measured using the first protractor element. The distal sole is then measured using third scale. Nominally repositioning the tool slightly to place the second sight ring in alignment with the center of rotation by providing equidistant measurement of the heel bulbs and bevel line using the fifth scale. Measuring the breakover distance using the fourth scale. Positioning the second sight ring at the lower extent of the palmar process. Measuring the palmar sole thickness using sixth scale. Measuring the angle of the fetlock using the second protractor element. Measuring the hoof—lamella zone with slight repositioning of the tool to place the measurement line in alignment with the dorsal extent of P3 allowing measurement to the dorsal hoof wall using dual scales. Slightly repositioning the tool placing forth scale between extensor process and coronet band and measuring the distance from the coronet band to the top of the extensor process.

DETAILED DESCRIPTION OF THE INVENTION

Figure 1:
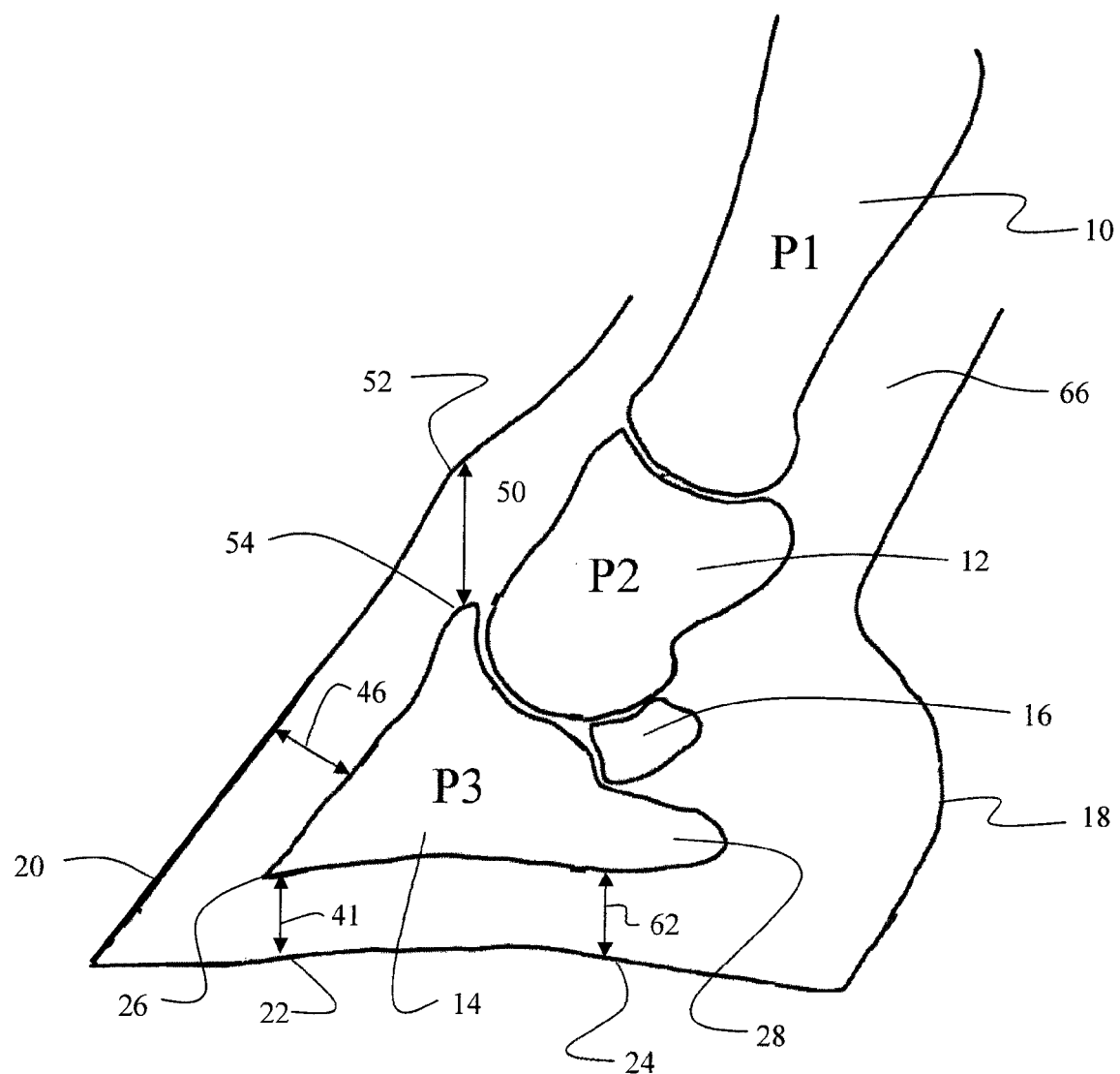
FIG. 1 is a section view of the parasagittal section of an equine foot comparable to a view provided by an x-ray of the foot.

FIG. 1 shows a section view of the structural elements of the parasagittal section of the foot of a horse. The principal skeletal structure includes the proximal phalanx or first pastern bone 10 (often designated as P1 in equine physiology literature), the middle phalanx or second pastern bone 12 (P2), the distal phalanx or coffin bone (sometimes referred to as the pedal bone) 14 (P3) and the navicular bone 16. The heel bulbs 18 define the posterior extent of the hoof while the dorsal wall 20 of the hoof forms the anterior extent. The sole of the foot and the frog generally, designated 22 and 24 respectively, constitute the lower extent of the foot which is surrounded by the hoof wall. The bottom of the hoof wall and the extremities of the frog form the surface of the hoof which contacts the ground and will be referred to nominally as the ground surface herein.

Conformation of the hoof is defined by a set of primary measurements. The palmar cortex (PC) is a distance measurement from the tip 26 of P3 to the articulation of the navicular bone. The palmar angle (PA) is a relative angle of the lower extent of P3 to the ground surface. The distal sole (DS) is the thickness of the sole at the tip of P3 to the ground surface while the palmar sole (PS) is the distance of the palmar process 28 from the ground surface. The break-over distance (B-O) is the distance from the tip of P3 to the break-over radius. The break-over radius changes based on growth of the hoof and is a primary measurement for determining the appropriate trimming of the hoof during care by a farrier. A tool and method to accurately accomplish break-over radius measurement during the shoeing process is defined in U.S. Pat. No. 7,165,623 entitled Farrier's Measuring Tool and Method for Using issued on Jan. 23, 2007 and having a common inventor with the present application.

Figure 2:
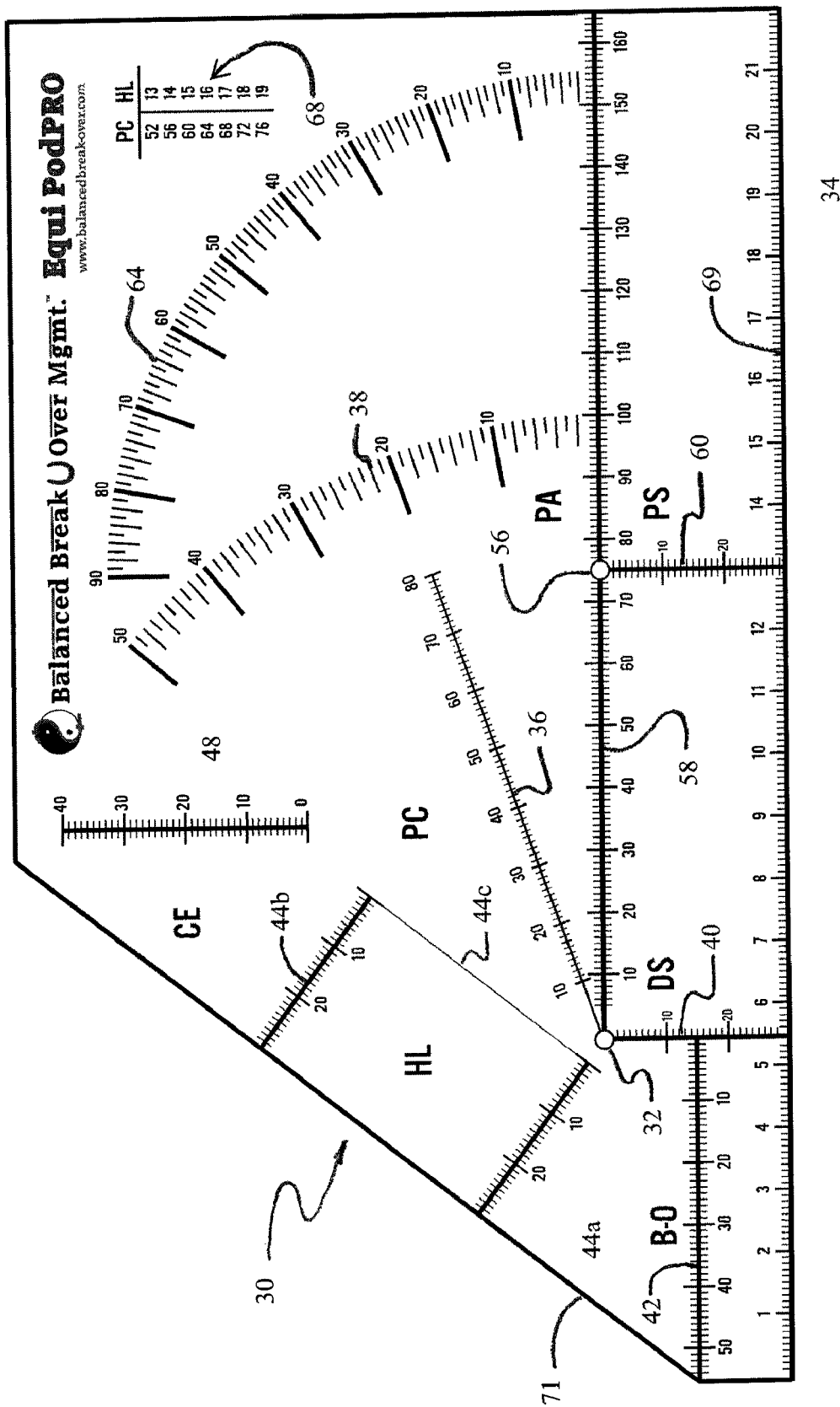
FIG. 2 is a front view of a tool employing the present invention.

A tool 30 incorporating the elements of the present invention is shown in FIG. 2. Multiple scales and protractor elements are positioned relative to two sight rings for measurement of the physical dimensions of an x-ray of an equine foot. Suitable material for manufacture of the tool is clear Lexan® or other substantially transparent material with sufficient rigidity and dimensional stability to retain accuracy of the measurements defined below. The relative positioning of the scales allows minimal movement of the tool to easily obtain all desired measurements. A first sight ring 32 provides an initial indicia for several measurements. The tool is positioned on an x-ray with the first sight ring placed over the tip of P3 and the bottom edge 34 is aligned parallel to the ground surface of the hoof. A first distance scale 36 extends posterior from the first sight ring at a selected angle of approximately 20° for measurement of the palmar cortex as will be described in greater detail subsequently with respect to FIG. 3. A first protractor element 38 centered on the first sight ring allows measurement of the palmar angle. A second distance scale 40 depending vertically from the first sight ring provides for measurement of the distal sole, the thickness 41 (as shown in FIG. 1) of the sole from the tip of P3 to the ground surface. Finally, a third distance scale 42 extends anterior from the second scale providing a measurement of break-over distance from the tip of P3. The third distance scale is offset downwardly from the first sight ring by a selected distance approximating the average distal sole to allow the scale to be positioned for the break-over distance measurement without significant movement of the tool.

A dual scale set 44a and 44b with a connecting measurement line 44c is positioned anterior upwardly from the first sight ring at a selected angle approximating the slope of the hoof dorsal wall for measurement of the hoof-lamella zone 46 (shown in FIG. 1) which extends between the dorsal extent of P3 to the dorsal wall of the hoof. The relative positioning of the dual scale set from the first sight ring again allows measurement with minimal movement of the tool. While shown in the embodiment in the drawings as a dual scale to enhance averaging of HL thickness over a length of the distal hoof wall, in alternative embodiments a single scale extending at the selected angle from the first sight ring.

A fourth distance scale 48 is spaced upward from and slightly posterior to the first sight ring and upward and posterior from the dual scale set. The fourth distance scale allows measurement of the spacing 50 from the coronet band 52 to the top of the extensor process 54 (generally designated as CE) (shown in FIG. 1). The fourth scale is substantially perpendicular to the ground surface approximating the relative position of the coronet band and extensor process in a normal equine foot. Positioning of the fourth distance scale again allows the CE measurement without significant movement of the tool from the initial positioning of the first sight ring on the P3 tip.

A second sight ring 56 is positioned posterior to the first sight ring parallel to the ground surface as a second indicia for desired measurements. A fifth distance scale 58 extends from the first sight ring through the second sight ring. For the embodiment shown, the second sight ring is placed approximately 75 mm from the first sight ring along the fifth distance scale as an approximation of the average distance from the center of rotation to the tip of P3. As disclosed in U.S. Pat. No. 7,165,263, previously referenced, the initial break-over line after fresh shoeing should be in approximate vertical alignment with the tip of P3 and be equidistant from the center of rotation with the posterior extent of the insertion of the frog at the heel bulbs. The second sight ring allows accurate measurement of the break-over line and heel bulbs from the center of rotation using the fifth distance scale.

A sixth distance scale 60 depends vertically from the second sight ring for measurement of the palmar sole (PS), the distance 62 (shown in FIG. 1) between the palmar process and the ground surface. The second sight ring allows minor adjustment of the tool for positioning over the lower extent of the palmar process for accurate measurement of the plamar sole with the sixth distance scale. Additionally, positioning of the second sight ring at the center of rotation as described above allows a consistent positioning for measurement of the palmar sole.

Figure 7:
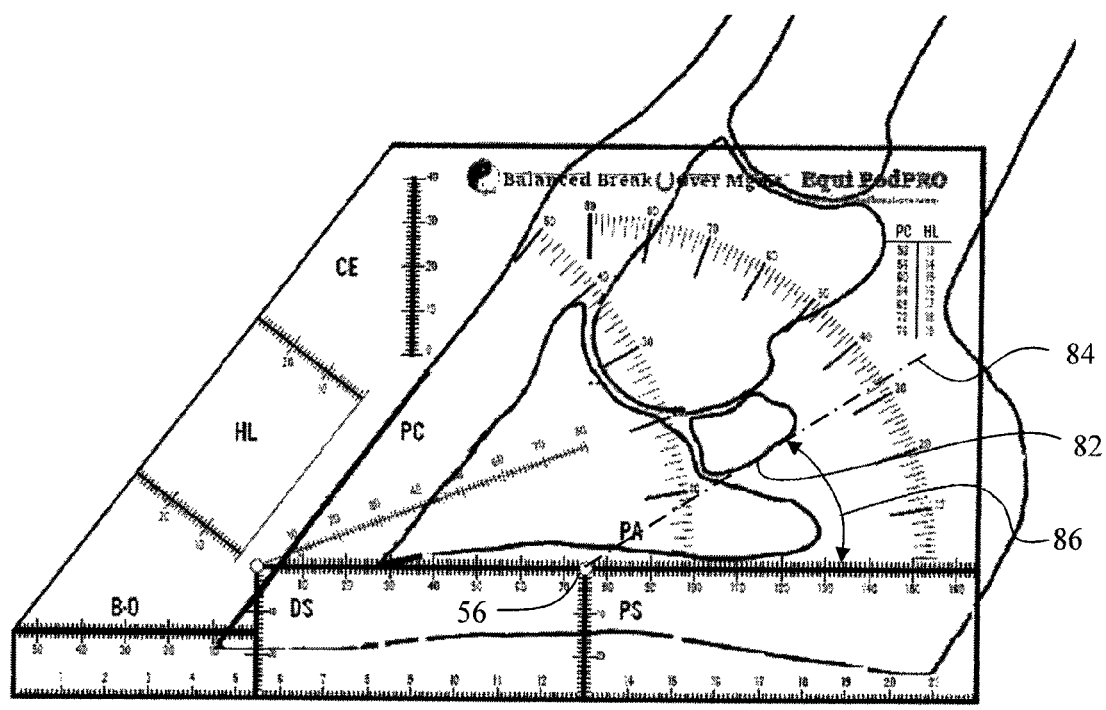
FIG. 7 is an overlay view of the tool positioned for measurement of the navicular tendon surface angle; and, FIG. 8 is an overlay view of the tool positioned for measurement of the P3 dorsal surface angle.
Figure 8:
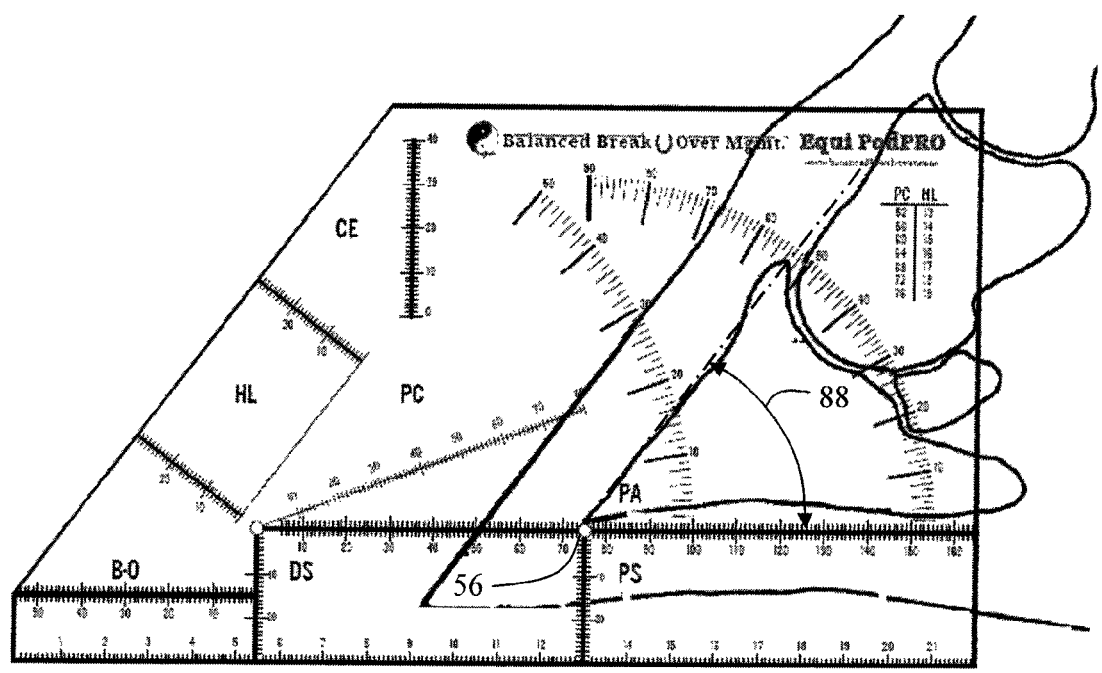

A second protractor element 64 centered on the second sight ring provides for measurement of general angles in the parasagittal section of the foot including, P1 or more generally the angle of the pastern 66 (shown in FIG. 1) relative to the ground surface, the dorsal angle of P3 and the angle of the navicular tendon surface as will be described in greater detail with respect to FIGS. 6, 7 and 8.

A comparison table 68 is printed on the tool for ease of reference regarding proper relationship between the palmar cortex (PC) distance and the hoof-lamella zone (HL) thickness wherein HL is nominally 25% if PC. The table provides a range of PC for horses of various sizes and the corresponding appropriate HL. Additionally, a seventh scale 69 is provided on the lower edge of the tool for general measurement tasks. A portion of left edge 71 of the tool is angled at a selected inclination approximating the average hoof angle in an equine with the dual scale extending perpendicularly therefrom for additional visual reference in aligning the tool substantially parallel to the distal hoof wall for measurements of the x-rayed structure.

Figure 3:
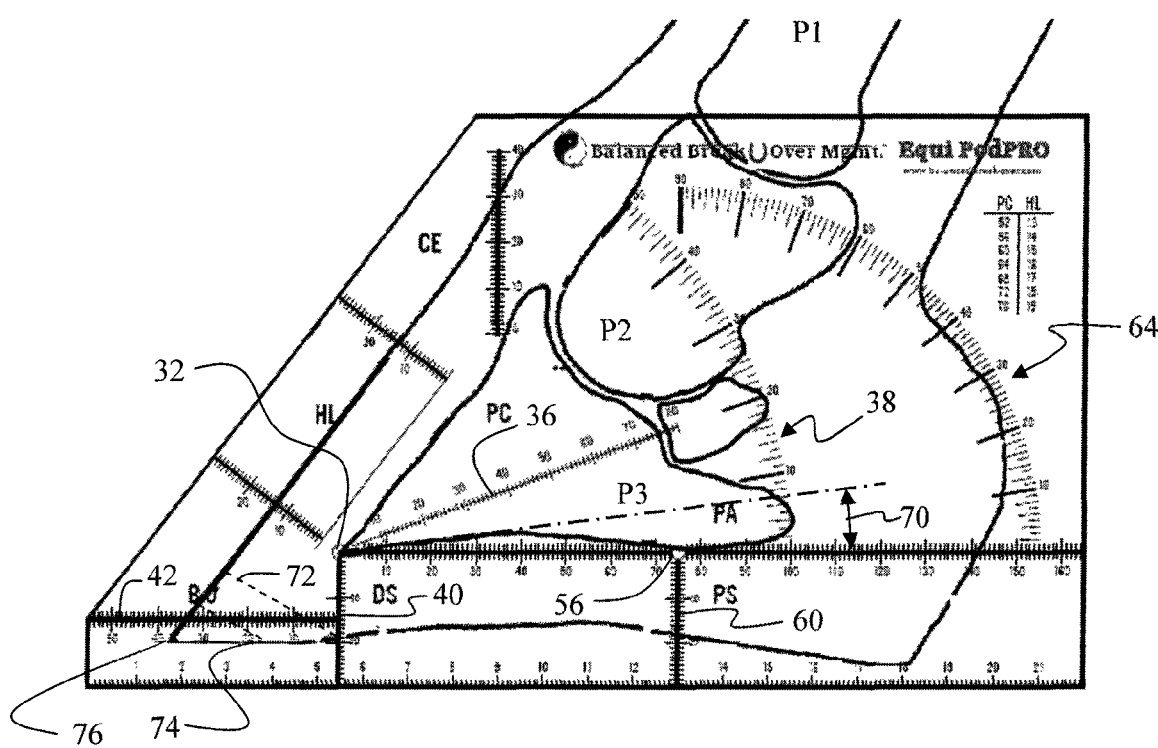
FIG. 3 is an overlay view of the tool of FIG. 2 positioned on an x-ray image comparable to FIG. 1 for a first set of measurements.
Figure 4:
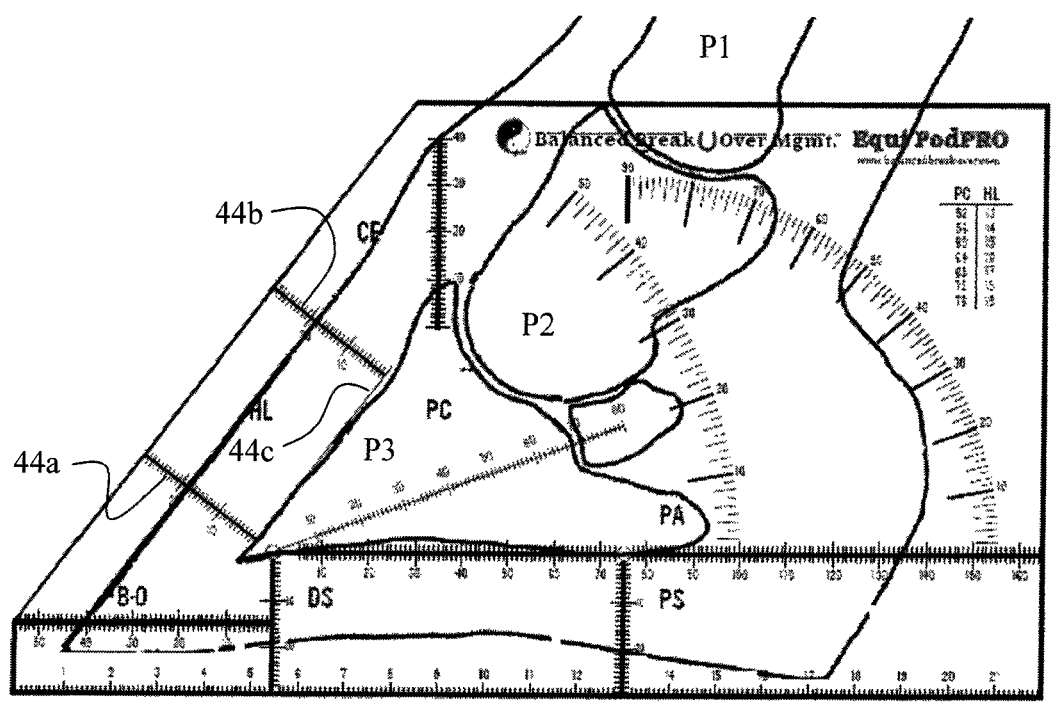
FIG. 4 is an overlay view of the tool positioned for hoof-lamella zone measurement.
Figure 5:
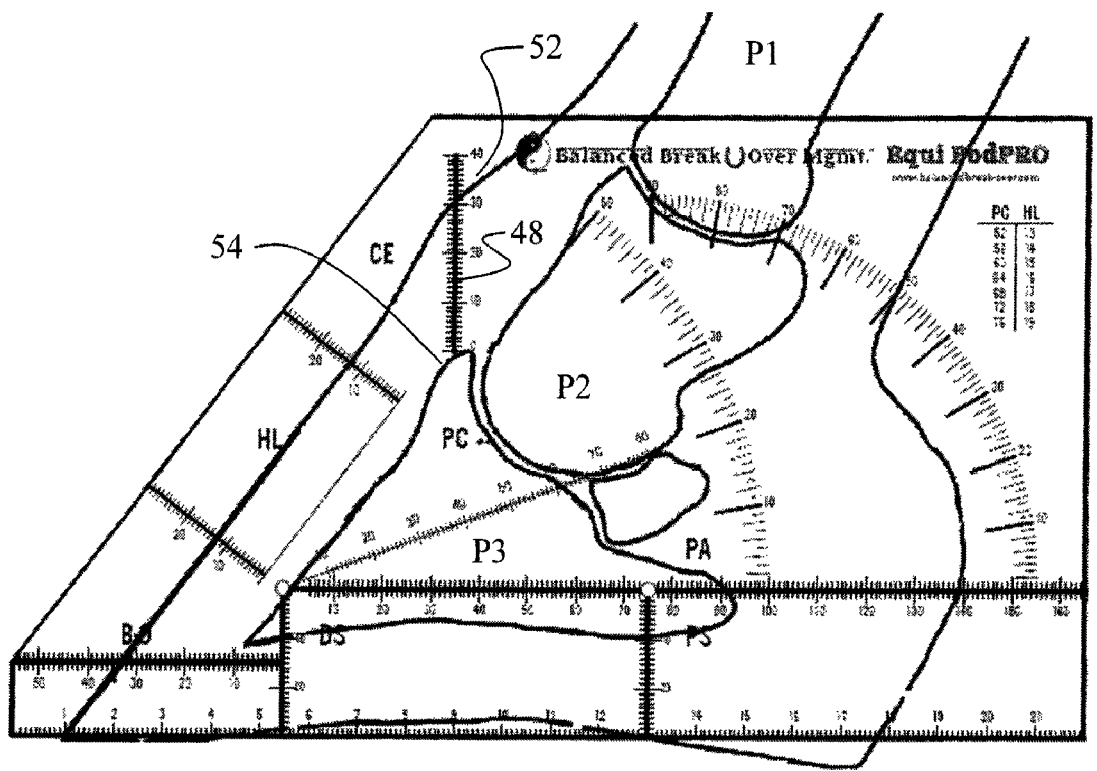
FIG. 5 is an overlay view of the tool positioned for coronet band to extensor process distance measurement.

FIGS. 3-5 demonstrate the use of the measurement elements provided by the tool of FIG. 2. Each figure represents an overlay of the tool on a representative x-ray taken of the parasagittal section of an equine foot. Referring to FIG. 3, the tool is positioned over the x-ray with the first sight ring aligned with the tip of P3 and the lower edge of the tool substantially aligned with the ground surface. In this position, the palmar cortex is measured using first scale 36. For the exemplary foot shown, PC is approximately 77 mm. The palmar angle is measured using first protractor element 38 resulting in measurement of an angle 70 of approximately 7° in the example shown, which would be consistent with a normal range of 3-9°. The distal sole is then measured using third scale 40 resulting in a 19 mm thickness for the example shown.

For the example shown, with little or no repositioning of the tool, the breakover distance is then measured using fourth scale 42. Nominally the tool would be repositioned slightly to place second sight ring 56 in alignment with the center of rotation by providing equidistant measurement of the heel bulbs and bevel line. The example shown provides for various stages of hoof growth with an initial bevel 72 directly below the first sight ring resulting in a measurement of 0 mm. After some period of hoof growth (nominally 6 weeks) the bevel 74 has been moved anterior to a break-over distance of approximately 15 mm. A hoof with growth potentially past a desirable break-over distance is shown with hoof tip 76 at a break-over distance of approximately 36 mm. With the second sight ring positioned at the lower extent of the palmar process, measurement of the palmar sole thickness is made using sixth scale 60. For the example a thickness of approximately 17-20 mm is obtained. Additionally, using second protractor element 64 an angle 78 of the fetlock is obtained, which for the example shown is approximately 68°.

Measurement of the hoof—lamella zone is accomplished with slight repositioning of the tool as shown in FIG. 4 to place measurement line 44c in alignment with the dorsal extent of P3 allowing measurement to the dorsal hoof wall using dual scales 44a and 44b. For the example shown, an HL of approximately 19 mm is shown. Using the PC/HL table provided on the tool, it can be seen that the HL is correct with an average PC of 76 indicating an HL of 19.

A measurement of the distance from the coronet band to the top of the extensor process is then accomplished by slight repositioning of the tool as shown in FIG. 5 placing forth scale 48 between extensor process 54 and coronet band 52 yielding a measurement for the example shown of approximately 31 mm.

Figure 6:
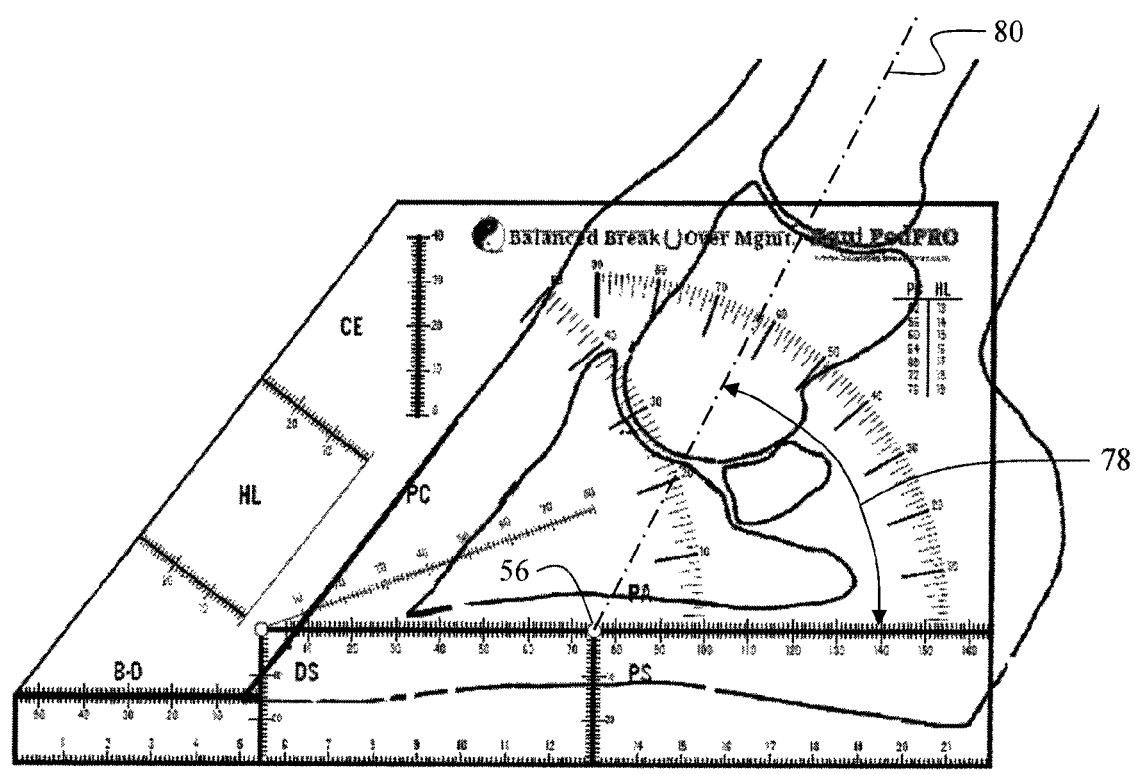
FIG. 6 is an overlay view of the tool positioned for measurement of pastern angle.

In FIG. 6, the tool is employed to measure the angle of the fetlock or specifically the centerline of P1. As shown, the fifth distance scale is oriented parallel to the ground surface and the second sight ring position to intersect a trace 80 drawn through the center of P1. Using second protractor element 64 an angle 78 of the fetlock is obtained, which for the example shown is approximately 68°. A similar measurement is made for the angle of tendon surface 82 of the navicular as shown in FIG. 7 by moving the tool slightly to center the second sight ring on a line 84 drawn through that surface, which for the example shown results in an angle 86 of 32°. Similarly, as shown in FIG. 8, re-centering the second sight ring on at the tip of P3 allows measurement of an angle 88 of the dorsal surface of P3, which for the example shown is approximately 53°

Having now described the invention in detail as required by the patent statutes, those skilled in the art will recognize modifications and substitutions to the specific embodiments disclosed herein. Such modifications are within the scope and intent of the present invention as defined in the following claims.

What is claimed is:

1. A tool for multidimensional measurement of x-rays of the parasagittal section of an equine foot comprising:
    a flat transparent overlay having a flat lower edge for parallel alignment with a ground surface;
    a first indicia for positioning of the tool over a tip of an image of a third phalanx;
    a first scale extending posterior at a selected angle from the first indicia;
    a second scale depending from the first indicia substantially perpendicular to the lower edge;
    a third scale extending anterior perpendicular to the second scale; and,
    a first protractor element centered posterior on the first indicia.

2. A tool as defined in claim 1 wherein the selected angle for the first scale is approximately 20°.

3. A tool as defined in claim 1 wherein the first indicia is a sight ring.

4. A tool as defined in claim 1 further comprising a lamella zone scale extending at a selected angle anterior to and radially from the first indicia.

5. A tool as defined in claim 4 wherein the lamella zone scale is a dual scale having a lower scale extending substantially radially from the first indicia and a parallel scale upwardly spaced from the lower scale, a measurement line extending between an origin on each of the lower and parallel scales.

6. A tool as defined in claim 5 wherein at least a portion of an anterior edge of the tool is angled at a selected inclination approximating a slope of an equine hoof distal wall as a visual indicator and the dual scale extends substantially perpendicular to the anterior edge.

7. A tool as defined in claim 1 further comprising a fourth scale upwardly displaced from the first indicia.

8. A tool as defined in claim 7 wherein the fourth scale is posterior to the first indicia and substantially perpendicular to the ground surface.

9. A tool as defined in claim 1 further comprising:
    a second indicia posterior to the first indicia and aligned therewith on a fifth scale having an origin at the first indicia, the fifth scale substantially parallel to the ground surface; and
    a sixth scale depending from the second indicia.

10. A tool as defined in claim 9 further comprising a second protractor element posterior to and centered on the second indicia.

11. A tool for multidimensional measurement of x-rays of the parasagittal section of an equine foot comprising:
    a flat transparent overlay having a flat lower edge for parallel alignment with a ground surface and at least a portion of an anterior edge angled at an inclination approximating a hoof distal wall;
    a first indicia for positioning of the tool over a tip of an image of a third phalanx;
    a first scale extending posterior at a selected angle of approximately 20° from the first indicia for measurement of a palmar cortex;
    a second scale depending from the first indicia substantially perpendicular to the lower edge for measurement of a distal sole thickness;
    a third scale extending anterior perpendicular to the second scale for measurement of a break-over distance;
    a first protractor element centered posterior on the first indicia for measurement of the palmar angle;
    a dual scale having a lower scale extending substantially radially from the first indicia and a parallel scale upwardly spaced from the lower scale, the dual scale extending substantially perpendicular to the angled anterior edge portion, a measurement line extending between an origin on each of the lower and parallel scales for measurement of a foot-lamella zone;
    a fourth scale upwardly displaced from the first indicia for measurement of a coronet band to extensor process distance, the fourth scale posterior to the first indicia and substantially perpendicular to the ground surface;
    a second indicia posterior to the first indicia and aligned therewith on a fifth scale having an origin at the first indicia, the fifth scale substantially parallel to the ground surface; and a sixth scale depending from the second indicia for measurement of a palmar sole thickness; and, a second protractor element posterior to and centered on the second indicia for measurement of a pastern angle.

12. A method for measuring physical parameters of the parasagittal section of an equine loot comprising the steps of:

taking an x-ray of the parasagittal section in a side view;

providing a tool having a flat transparent overlay with a flat lower edge for parallel alignment with a ground surface and at least a portion of an anterior edge angled at an inclination approximating a hoof distal wall;

a first sight ring for positioning of the tool over a tip of an image of a third phalanx;

a first scale extending posterior at a selected angle of approximately 20° from the first sight ring for measurement of a palmar cortex;

a second scale depending from the first sight ring substantially perpendicular to tile lower edge for measurement of a distal sole thickness;

a third scale extending anterior perpendicular to the second scale for measurement of a break-over distance;

a first protractor element centered posterior on tile first sight ring for measurement of the palmar angle;

a dual scale having a lower scale extending substantially radially from tile first sight ring and a parallel scale upwardly spaced from the lower scale, the dual scale extending substantially perpendicular to the angled anterior edge portion, a measurement line extending between an origin on each of the lower mid parallel scales for measurement of a hoof-lamella zone;

a fourth scale upwardly displaced from the first sign ring for measurement of a coronet band to extensor process distance, the fourth scale posterior to the first sight ring and substantially perpendicular to the ground surface;

a second sight ring posterior to the first indicia, mid aligned therewith on a fifth scale having an origin at the first sight ring, the fifth scale substantially parallel to the ground surface;

a sixth scale depending from the second sight ring for measurement of a palmar sole thickness; and, a second protractor element posterior to arid centered on the second sight ring for measurement of a pastern angle;

positioning the tool over the x-ray with the first sight ring aligned with the tip of P3 and the lower edge of the tool substantially aligned with the ground surface:

measuring the palmar cortex using first scale;

measuring the palmar angle using the first protractor element;

measuring the distal sole using the third scale;

nominally repositioning the tool slightly to place the second sight ring in alignment with the center of rotation by providing equidistant measurement of the heel bulbs and bevel line using the fifth scale;

measuring the breakover distance using the fourth scale;

positioning the second sight ring at the lower extent of the palmar process;

measuring the palmar sole thickness using the sixth scale;

measuring the angle of the fetlock using the second protractor element;

measuring the hoof-lamella zone with slight repositioning of the tool to place the measurement line in alignment with the dorsal extent of P3 allowing measurement to the dorsal hoof wall using the dual scales;

slightly repositioning of the tool placing the forth scale between extensor process and coronet band; and, measuring the distance from the coronet band to the top of the extensor process.

* * * * *